United States Patent [19]

Malen et al.

[11] 4,080,452

[45] Mar. 21, 1978

[54] N-ACYL ANILINES, USEFUL FOR GASTRO-ENTEROLOGICAL DISORDERS

[75] Inventors: Charles Malen, Fresnes; Pierre Roger, St. Cloud; Xavier Pascaud, Paris, all of France

[73] Assignee: Science Union et Cie, Societe Francaise de Recherche Medicale, Suresnes, France

[21] Appl. No.: 656,553

[22] Filed: Feb. 9, 1976

[30] Foreign Application Priority Data

Feb. 14, 1975 United Kingdom ............... 6294/75

[51] Int. Cl.² ............... A61K 31/535; C07D 295/00
[52] U.S. Cl. ........................ 424/248.54; 260/293.75; 260/293.79; 260/326.4; 260/326.43; 260/307 R; 260/453 AP; 260/562 N; 424/267; 424/272; 424/274; 424/324; 544/163; 544/165

[58] Field of Search ............... 260/247.2 A, 453 AP, 260/562 N; 424/248.54; 544/163, 165

[56] References Cited

U.S. PATENT DOCUMENTS

| | | | |
|---|---|---|---|
| 2,912,460 | 11/1959 | Ehrhart et al. | 260/247.2 A X |
| 3,989,834 | 11/1976 | Malen et al. | 260/562 N X |

*Primary Examiner*—Leonard Schenkman
*Attorney, Agent, or Firm*—Omri M. Behr

[57] ABSTRACT

This invention relates to novel N-acyl anilines, to a process for their preparation and to pharmaceutical compositions containing them. The N-acyl anilines are obtained by condensing a substituted aniline with an aminolower alkyl carboxylic acid or a functional derivative thereof.

The compounds of the invention have therapeutic utility namely in the gastro-enterologic field.

8 Claims, No Drawings

N-ACYL ANILINES, USEFUL FOR GASTRO-ENTEROLOGICAL DISORDERS

DESCRIPTION OF THE PRIOR ART

The prior art may be illustrated with the French Pat. application published with the No. 2.264.526 to the same assignee. This application relates to p. substituted N-acyl anilines.

SUMMARY OF THE INVENTION

This invention relates to ortho alkoxy meta $R_2$ substituted anilides substituted on the aminogroup with an amino lower alkyl carboxylic residue. They have the formula

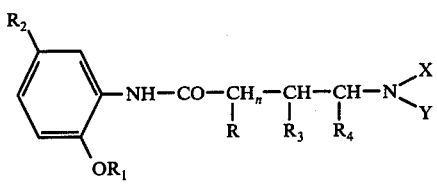

in which
n is zero or an integer from one to three,
R represents a hydrogen atom or a lower alkyl radical
$R_1$ represents a lower alkyl radical, a lower alkenyl radical, a lower phenyl-alkyl radical or a lower cyclo-alkyl radical
$R_2$ represents a grouping having an electrophilic character selected from the group consisting of a cyano, a trifluoromethyl and a lower acyl residue
$R_3$ represents a hydrogen atom or a lower alkyl radical,
$R_4$ represents a hydrogen atom or a lower alkyl radical,
X and Y, which may be the same or different, each represents a lower alkyl radical or X and Y together with the nitrogen atom to which they are attached form a saturated heterocycle optionally containing one or two other hetero-atoms and having from 3 to 7 ring members, or X and $R_3$ together form an alkylene chain having from 2 to 4 carbon atoms optionally containing one or two hetero-atoms.

The present invention also provides salts of the compounds of the general formula I with inorganic and organic acids, preferably a pharmacologically compatible inorganic or organic acid.

When the amino alkyl carboxylic side chain contains at least one asymetric carbon, the compounds may be resolved into their optically-active isomers.

These compounds may be produced by acylating an ortho-substituted aniline with a lower alkyl carboxylic acid bearing at the end of the carbon chain an amino group or a substituent which may be easily split.

This invention relates to the pharmaceutical compositions incorporating as active ingredient at least one compound of the formula I or a salt thereof with an inert nontoxic pharmaceutical carrier.

This invention also relates to a method for treating or preventing gastric ulcers due to gastric hypersecretion or delay in gastric evacuation which consists in administering to warm-blooded animals suffering from said aliments a small but efficient amount of a compound of the formula I or a salt thereof, or to warm-blooded animals disposed to suffer from said aliments a small but efficient amount of a compound of the formula I or a salt thereof.

PREFERRED EMBODIMENTS

This invention relates to novel N-acyl anilines, to a process for their preparation and to pharmaceutical compositions containing them.

The present invention provides more specifically N-acyl anilines of the general formula

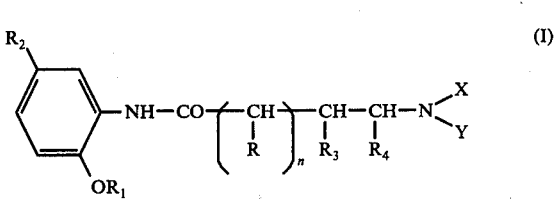

in which
n is zero an integer from one to three,
R represents a hydrogen atom or a lower alkyl radical,
$R_1$ represents a lower alkyl radical, a lower alkenyl radical, a phenyl lower alkyl radical or a lower cycloalkyl radical
$R_2$ represents a grouping having an electrophilic character selected from the group consisting of a cyano, a trifluoromethyl and a lower acyl residue
$R_3$ represents a hydrogen atom or a lower alkyl radical
$R_4$ represents a hydrogen atom or a lower alkyl radical
X and Y, which may be the same or different, each represents a lower alkyl radical or X and Y together with the nitrogen atom to which they are attached form a saturated heterocycle optionally containing one or two other hetero-atoms and having from 3 to 7 ring members, or X and $R_3$ together form an alkylene chain having from 2 to 4 carbon atoms or X and $R_4$ together from an alkylene chain having from 2 to 4 carbon atoms optionally containing one or two hetero-atoms.

Especially preferred is the embodiment of formula I(a)

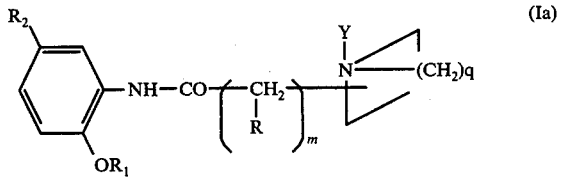

wherein R, $R_1$ are as above, $R_2$ is cyano, trifluoromethyl or lower alkanoyl, said $R_1$ groups in these compounds being considered in this context as functionally equivalent Y is lower alkyl, m is 0 or an integer of 1 to 5 and q is 0 or an integer of 1–5 most suitably 2–5 giving rise to piperidine, pyrrolidine, hexamethylene imine or hexahydroazocine moieties, said heterocyclic rings varying by a small number of methylene groups are to be considered in this context as functionally equivalent.

The present invention also provides salts of the compounds of the general formula I with inorganic and organic acids, preferably a pharmacologically compatible inorganic or organic acid.

The term "lower alkyl" is used above to denote a linear or branched saturated hydrocarbon chain having from 1 to 6 carbon atoms, for example, a methyl, an ethyl, an isopropyl or a tertiary butyl radical.

The term "lower alkenyl" is used above to denote a hydrocarbon chain containing a carbon-carbon double bond, and having from 2 to 6 carbon atoms, for example an allyl or a pentenyl radical.

The term "lower cycloalkyl" denotes a cyclic saturated structure, which may be substituted be one or more lower alkyl radical having from 3 to 7 ring atoms such as a cyclopropyl, a 2,2-dimethyl cyclopropyl or a cyclohexyl radical.

The term "lower acyl residue" denotes an acyl residue derived from a lower alkanoic acid, such as an acetyl radical, a propionyl radical or a butyryl radical.

When X and Y, or X and $R_3$, or X and $R_4$, together form an alkylene chain, the rings so formed are preferably a piperidine, a pyrrolidine, a hexamethylenimine or a hexahydroazocine rings. These alkylene chains can be interrupted by a hetero-atom for example, nitrogen, sulphur or oxygen, resulting in an oxazolidine, thiazolidine, morpholine, thiamorpholine, homomorpholine, imidazolidine, isoxazolidine or tetrahydro-oxazine ring.

They also may be substituted by one or more alkyl radicals.

Amongst the compounds of the present invention, there may be mentioned more especially:

1-(N-methyl-piperid-2-yl)-acetylamino-2-methoxy-5-trifluoromethyl-benzene; and its hydrochloric acid addition salt 1-(N-ethyl-piperid-3-yl-carboxamido)-2-methoxy-5-trifluoromethyl-benzene;

1-(β-morpholinyl propionylamino)-2-methoxy-5-cyano-benzene;

1-(β-pyrrolidinyl-methyl propionylamino)-2-methoxy-5-acetyl-benzene.

1-(β-piperidino propionylamino) 2-methoxy 5)cyano benzene 1-(NN-diethylamino propionylamino) 2-methoxy 5-cyano benzene 1-(β-pyrrolidinyl propionylamino) 2-methoxy 5-cyano benzene 1-(NN-dimethylamino propionylamino) 2-methoxy 5-cyano benzene The compounds of the present application exhibit valuable pharmacological properties. They exert a strong effect on the gastric evacuation and a strong inhibitory effect on the gastric secretion. Moreover they show a very slight, if any, depressive action on the central nervous system. They do not possess anti-emetic effect. They show further a very low toxicity.

Because of these benefitful properties they may be used in human or animal therapy, and especially in gastroenterology, for the prevention or treatment of digestive disorders or ulcers connected with gastric hypersecretion and delay in the gastric evacuation.

The present invention therefore also provides pharmaceutical compositions comprising, as active ingredient, at least one compound of the general formula I in the free form or in the form of a salt, in admixture or conjunction with an inert pharmaceutical excipient.

The compositions are in a form suitable for oral, parenteral, rectal, perlingual or percutaneous administration, as for example, uncoated or coated tablets, injectable suspensions or solutions packaged in ampoules, in multi-dose bottles or in self-injectable syringes, suppositories, sublingual tablets or solutions for percutaneous use.

Their posology may vary depending on the age of the patient, the therapeutic requirements and the method of administration. It may range especially between 20 and 400 mg per day and from 10 to 200 mg per unit dosage.

The present invention also provides a process for the preparation of the compounds of the general formula I which comprises condensing an o-alkoxy-aniline of the general formula

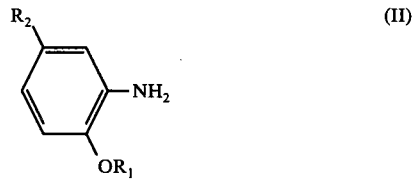

in which $R_1$ and $R_2$ have the meanings given above, with an amino-alkyl-carboxylic acid of the general formula

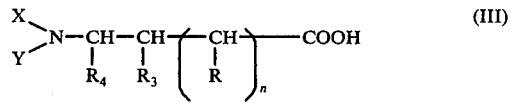

in which R, $R_3$, $R_4$, X, Y and n have the meanings given above, or with a functional derivative thereof, to form an anilide of the general formula

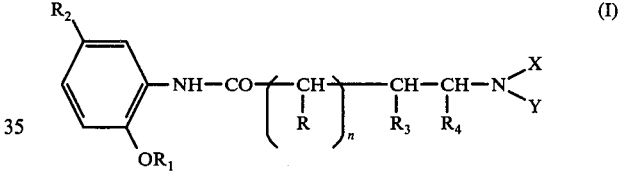

The compounds of the general formula I possess at least one basic group and can be salified by addition of an inorganic acid, for example, hydrochloric acid, sulphuric acid, nitric acid, phosphoric acid, formic acid, butyric acid, benzoic acid, nicotinic acid, tartaric acid, glucose-1-phosphoric acid, embonic acid and ethane-sulphonic acid.

When the amino-alkyl-carboxylic acid portion possesses at least one asymmetric carbon atom, it may be possible to resolve the compound of the general formula I into its optical isomers by forming a salt with an optically-active organic acid. Amongst the acids which are most suitable for such resolution, there may be mentioned d- and l-tartaric acids, d- and l-camphoric acids, N, N-dimethyl -d- and -l-tartramic acids and optically-active bisnaphtyl-phosphoric acid.

As the starting material, for the process of the present invention, it is also possible to use an amino-alkylcarboxylic acid of the formula II which has already been resolved. The anilide of the general formula I produced is thus in an optically-active form. It can also be advantageous to resolve the molecule at the stage of the compound I by means of the same reagents as those listed above.

According to a preferred method of carrying out the process according to the present invention, (a) the functional derivative of the amino-alkyl-carboxylic acid of the formula III is an acid halide, the anhydride, a mixed anhydride or an alkyl, aryl or aralkyl ester;

(b) the mixed anhydride is preferably formed in situ with a dehydrating reagent, for example, a dicycloalkyl-carbodiimide, ethoxy-acetylene, a cyanogen halide or carbonyldiimidazole;

(c) the condensation is carried out by employing, as the functional derivative of the acid of the general formula III, an acid halide, for example the acid chloride, in the presence of an acid acceptor, for example, an inorganic base, such as sodium carbonate, a trialkylamine, such as triethylamine, a pyridyl base, such as pyridine or collidine, dimethyl-aniline or an excess of the substituted aniline of the general formula II;

(d) the condensation is carried out in an inert solvent, for example, a halogenated solvent, a linear or aliphatic ether, an alkane-nitrile, an aromatic hydrocarbon, for example toluene or xylene, a tertiary alcohol, for example tertiary butanol or tertiary amyl alcohol, or an aprotic polar solvent for example dimethylformamide or hexaphosphorotriamide;

The invention further provides another process for producing the compounds of general formula I in which X and Y are each a lower alkyl radical or X and Y together with the nitrogen atom to which they are attached form a saturated heterocycle optionnally containing one or two other heteroatoms and having from 3 to 7 ring members, which consits in reacting a substituted aniline of general formula II with an ω-substituted alkanoic acid of the formula IV

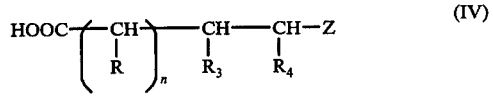
(IV)

in which R, $R_3$ and $R_4$ are defined as above given and Z is a substituent which may be easily split selected from the group comprising an arylsulphonyloxy radical, a lower alkyl sulphonyloxy radical, a halogen and a trialkyl silyloxy radical or a functional derivative thereof, to produce a substituted anilide of the formula V

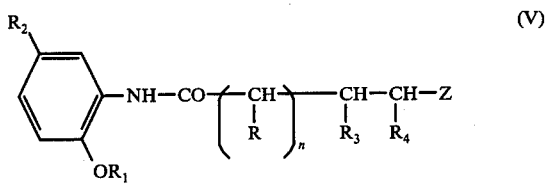
(V)

and condensing the latter with an amino derivative of the formula VI

(VI)

in which X and Y, which may be the same or different, each represents a lower alkyl radical or X and Y together with the nitrogen atom to which they are attached, form a saturated heterocycle, optionnally containing one or two heteroatoms and having from 3 to 7 ring atoms, and recovering a compound of general formula I

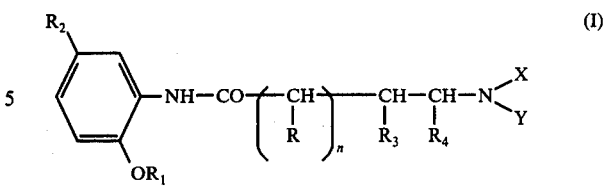
(I)

in which $R_1$, $R_2$, $R_3$, $R_4$ and $n$ are defined as previously given and X and Y have the meanings here-above specified which may be further, when desired, salified by addition of a mineral or organic acid or resolved when the aminoacyl side-chain includes at least one asymetric carbon atom.

Preferably the substituent Z in the compounds of general formula IV is a halogen such as a fluorine or chlorine atom, in the presence or absence of an alkali-metal iodide. It may also be a methane sulphonyloxy radical, a.p. toluenesulphonyloxy radical or a naphtylsulphonyloxy radical. The reaction between a compound of general formula IV and the substituted aniline of general formula II is performed in an inert organic solvent such as halogenated alkane, a lower alkane nitrile such as acetonitrile, a nitroalkane such as nitromethane, a lower alkyl ketone such as acetone, methyl ethylketone or methylisobutylketone, a linear or cyclic ether such as ethyl or isopropyl ether or tetrahydrofuran; an organic base such as pyridine, dimethylaniline or 4-dimethylaminopyridine; a polar aprotic solvent such as dimethyl formamide, dimethyl acetamide, hexamethyl phosphoramide, divinyl sulfone or dimethylsulphoxide.

The compound of general formula IV may be the free acid or a salt thereof or preferably a functional derivative thereof such as a halide, a lower alkyl or an aryl ester, the anhydride or a mixed anhydride. The halide may be formed "in situ" by contacting the free acid with an halogenating reagent such as thionyl chloride in a polar solvent such as hexamethyl phosphoramide.

The functional derivative may also be the mixed anhydride formed in situ by reacting the free acid of general formula IV with a dehydrating agent such as a dialkyl or dicycloalkyl carbodimide, ethoxy acetylene or carbonyldiimidazole.

The reaction between the compound of formula V and the amino derivative of formula VI is preferably carried out in a polar solvent such as a pyridine base or dimethylformamide or in an aromatic hydrocarbon such as benzene, toluene or xylene.

The starting materials of formula II are obtained according to the methods known from the literature, namely by submitting an O. aminophenol of the formula

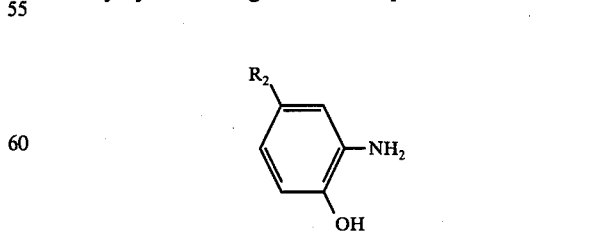

in which $R_2$ has the previously given meanings, to the action of an alkylating agent, an alkenylating agent, a cycloalkylating agent or a phenyl lower alkylating agent.

The following examples are merely intended to illustrate the invention.

The melting points and the temperatures are expressed in degrees Centigrades.

EXAMPLE I 1-(βmorpholinylpropionylamino) 2-methoxy 5-cyano benzene step A

1-(β-chloropropionylamino) 2-methoxy 5-cyanobenzene 12.5 g of 2-methoxy 5-cyano aniline obtained according to the method described by Blanksma and Petri Rec. Trav. Chim. 66 (1947) 365–373 are dissolved in 100 ml benzene and 8.6 g triethylamine are added, then 10.7 g of β-chloropropionyl acid chloride dissolved in 40 ml benzene. The mixture is kept at room temperature for 12 hours. The thus-appeared precipitate is thereafter filtrated, washed with water and dried. The compound is recrystallised from a mixture of methylene chloridehexane. After usual purifications it melts at 137°–141°.

Analysis $C_{11}H_{11}ClN_2O_2 = 238.67$

|  | C% | H% | N% | Cl% |
|---|---|---|---|---|
| Calculated | 55.83 | 4.65 | 11.74 | 14.87 |
| Found | 55.33 | 4.58 | 11.68 | 14.57 | step B

1-(β-morpholinylpropionylamino) 2-methoxy5-cyanobenzene

In 50 ml toluene 5 g of potassium carbonate and 4,4 g of 1-(β-chlopropionylamino) 2-methoxy 5-cyanobenzene obtained at step A are suspended, then 1.6 g morpholine is added dropwise. The suspension is heated to reflux for 15 hours. The precipitate is then separated by filtration and washed twice with few ml of toluene. The toluenic phases are united and kept in a cold place where the morpholino derivative begins to crystallize. After two hours standing, the crystals are suction-filtered, dried, washed with cold toluene and dried in an oven.

The compound is further purified by chromatography on silica and elution with a mixture of chloroform-methanol. From the eluate the 1-(β-morpholinylpropionyl amino) 2-methoxy 5-cyanobenzene crystallises, melting at 148°–150°.

On T L C the compound appears homogeneous

Analysis $C_{15}H_{19}N_3O_3 = 289.3$

|  | C% | H% | N% |
|---|---|---|---|
| Calculated | 62.28 | 6.62 | 14.53 |
| Found | 63.02 | 6.81 | 14.08 |

In the same manner and starting from 1-(β chloropropionylamino) 2-methoxy 5-cyanobenzene and the corresponding amino compound they are respectively obtained:

- 1-(dimethylaminopropionylamino) 2-methoxy 5-cyanobenzene MP 128°–132°
- 1-(diethylaminopropionylamino) 2-methoxy 5-cyanobenzene MP 237°–240° (at its hydrochloride)
- 1-(β-piperidinopropionylamino) 2-methoxy 5-cyano benzene MP 136°–140°
- 1-(β-pyrolidinylpropionylamino)2-methoxy 5-cyano benzene MP 106°–108°
- 1-(β-oxazolidinylpropionylamino) 2-methoxy 5-cyanobenzene
- 1-(N ethyl N-butylaminopropionylamino) 2-methoxy 5-cyanobenzene

EXAMPLE II 1-(β-pyrrolidinylα-methylpropionylamino) 2-methoxy 5-acetyl benzene step A

1-(β-chloroα-methyl propionylamino) 2-methoxy 5-acetyl benzene 24.8 g of 2-methoxy 5-acetyl aniline [obtained according to Oelschager Arzneimit. Forschung 8 532–539 (1958)] dissolved in 150 ml benzene are added with 10.6 g of 3-chloro isobutyric acid chloride in 40 ml benzene. The mixture is kept at room temperature for 2 hours under stirring then diluted with 250 ml water. The benzenic phase is separated. The aqueous phase is extracted twice with benzene. The benzenic solutions are united, washed with 2N hydrochloric acid and then with water, dried on sodium sulphate, filtered and evaporated to dryness. The residue is recrystallised from isopropyl ether from which 15.5 g of pure compound are recovered (yield = 77%) -1-(β-chloroα-methyl propionylamino) 2-methoxy 5-acetylbenzene melts at 92°–97°.

Analysis $C_{13}H_{16}ClNO_3 = 269.7$

|  | C% | H% | N% | Cl% |
|---|---|---|---|---|
| Calculated | 57.90 | 5.98 | 5.20 | 13.15 |
| Found | 58.15 | 6.04 | 5.47 | 13.34 | step B

1-(β-pyrrolidinyl α-methyl propionylamino) 2-methoxy 5-acetylbenzene 8 g of 1-(β-chloro α-methyl propionylamino) 2-methoxy 5)acetylbenzene are dissolved in 90 ml benzene. To the solution 1.8 g of anhydrous potassium carbonate are added then dropwise 12. g of pyrrolidine. The whole mixture is refluxed for 5 hours then filtered. The precipitate is washed twice with toluene. The united toluenic solutions are distillated off and the dry residue is taken up in an ethereous solution of hydrochloric gas. The hydrochloride precipitates and is purified by crystallising it from aceto-nitrile. The pure compound melts at 115°–140° (with decomposition).

Analysis $C_{17}H_{24}N_2O_3,ClH = 340.8$

|  | C% | H% | N% | Cl% |
|---|---|---|---|---|
| Calculated | 59.91 | 7.40 | 8.23 | 10.41 |
| Found | 59.63 | 7.50 | 8.13 | 10.37 |

In the same manner but replacing pyrrolidine with the corresponding amine the following compounds are respectively obtained

- 1-(β-dimethylamino α-methyl propionylamino) 2-methoxy 5-acetylbenzene
- 1-(β-diethylamino α-methyl propionylamino) 2-methoxy 5-acetylbenzene
- 1-(β-morpholinyl α-methylpropionylamino) 2-methoxy 5-acetyl benzene
- 1-(β-piperidyl α-methylpropionylamino) 2-methoxy 5-acetylbenzene
- 1-(β-diisopropylamino α-methylpropionylamino) 2-methoxy 5-acetyl benzene

EXAMPLE III 1-(N-methylpiperidyl-2) acetylamino 2-methoxy 5-trifluoromethylbenzene and its hydrochloride step A (N-methylpiperidyl-2) acetic acid hydrochloride 77 g ethyl (N-methylpiperidyl-2) acetate hydrochloride obtained according to the method described by Sperber J. Of. Am. Chem. Soc. 81 704–709 (1959) are dissolved in 730 ml of 6 N hydrochloric acid and the mixture is refluxed for 3 hours. The solvent is distilled off and the dry residue is taken up in hot acetonitrile. In the cold the crystallisation initiates and after 4 hours standing the crystalls are separated, washed and dried under reduced pressure.

72.1 g of (N-methylpiperidyl-2) acetic acid hydrochloride are recovered i.e. a yield of 91%, melting at 160°–185° (with decomposition)

| Analysis $C_8H_5NO_3ClH = 193.67$ | | | | |
|---|---|---|---|---|
| | C% | H% | N% | Cl% |
| Calculated | 49.61 | 8.33 | 7.23 | 18.30 |
| Found | 49.43 | 8.16 | 7.27 | 18.29 |

10 g of the hydrochloride obtained at step A are dissolved in 380 ml hexamethylphosphorotriamide then dropwise 3.8 ml freshly distilled thionyl chloride are added. The mixture is kept aside for 4 hours at room temperature then added with 9.9 g 2-methoxy 5-trifluoromethyl aniline-obtained according to Porai-Koshits Zh. Priklad Kh. 28 969–973 (1955). The reaction medium is kept under stirring for a night at ambient temperature, thereafter diluted with ethyl ether-1- (N-methylpiperidyl-2) acetyl amino 2-methoxy 5-trifluoromethyl benzene (hydrochloride) precipitates which is filtered, washed with ether and dried. The pure compound is obtained by recrystallization from ethanol, then from water. It melts at 166°–184° (with decomposition)

| Analysis $C_{16}H_{21}F_3N_2O_2ClH + 4.5\%$ water = 366.8 | | | |
|---|---|---|---|
| | C% | H% | N% |
| Calculated | 52.39 | 6.05 | 7.64 |
| Found | 52.19 | 5.98 | 7.82 |

In the same manner but starting from (N-methylpiperidyl-2) acetic acid hydrochloride and the substituted 5-trifluoromethylanilines, the following anilides are obtained:

1-[(N-methylpiperidyl-2) acetylamino] 2-ethoxy 5-trifluoromethylbenzene

1-[(N-methylpiperidyl-2) acetylamino] 2-allyloxy 5-trifluoromethylbenzene

1-[(N-methylpiperidyl-2) acetylamino] 2-cyclopropyloxy 5-trifluoromethylbenzene

In the same manner starting from (N-ethylpyrrolidinyl-2) acetic acid and 2-methoxy 5-trifluoromethyl aniline, 1-[(N-ethylpyrrolidinyl-2) acetylamino] 2-methoxy 5-trifluoromethyl benzene is obtained Starting from (N-ethylpiperidyl-3) carboxylic acid and 2-methoxy 5-trifluoromethyl aniline, 1-[(N-ethylpiperidyl-3) carboxamido] 2-methoxy 5-trifluoromethyl benzene is obtained.

The required 2-alkoxy or 2-alkenyloxy or 2-cyclopropyloxy 5-trifluoromethyl derivatives when they are not yet known are obtained from 2-chloro or 2-fluoro 5-trifluoromethyl 1-nitrobenzene by reacting the corresponding alkanol, hydroxy alkene or hydroxy cyclopropane followed by reduction of the nitro froup by means of catalytic hydrogenation as described by J. H. Brown J. Chem. Soc. (suppl.I) 1949, 895

PHARMACOLOGICAL STUDY OF THE COMPOUNDS ACCORDING TO THE INVENTION (a) Acute toxicity The acute toxicity of the compounds of the invention was determined on lots of mice (Rockland strain) weighing from 18 to 22 g. Each compound is administered intra peritoneously or perorally at increasing dosis. The deaths if any, are recorded. After eight days of maintenance the total number of deaths is determined. The average letal dosis is then graphically calculated. Depending on the compounds it range from 250 to 500 mg/kg. Comparatively the $LD_{50}$ (intraperitoneously) of Metoclopramide is comprised between 125 and 250 mg/kg.

(b) Effect on gastric evacuation

The stimulating effect on gastric evacuation was determined by the method of Brodie (Fed. Proc. 25 (1965) 714).

In this method the speed at which pellets of Amberlite of regular shape and previously introduced by tubing into the stomach, are expelled, is determined on groups of rats fasted for 12 hours.

The compounds to be tested are administered by subcutaneous or oral way and the avery active dosis which is the minimal dosis which increases of 50% the gastric evacuation has been found from 2mg/kg to 30mg/kg.

In comparison thereof 1-(N-ethylpyrrolidin-2yl) acetyl 2-methyl 5-sulphamoyl aniline selected as a reference compound had a $ED_{50}$ of 44mg/kg.

(c) Effect on gastric secretions

The inhibitory effect on gastric secretions was determined on groups of rats using the method described by H. G. Shay and coll. The gastric secretions are collected 4 hours after ligature of the pylorus and the total acidity thereof is determined by means of an Autopipetting system Radiometer (titration by 0.1 N NaOH until pH = 8.45)

The tested doses administered intraperitoneally or intraduodenally ranged from 1 to 30mg/kg. The $ED_{50}$ is from about 2mg/kg to about 10mg/kg. In similar experimental conditions, at a dose of 30mg/kg, neither 1-(N-ethylpyrrolidin-2yl) acetyl 2-methoxy 5-sulphamoyl aniline nor Metoclopramide show any effect on the gastric secretions.

EXAMPLE IV

Tablets containing 20 mg of 1-[β-morpholinylpropionylamino]-2-methoxy 5-cyano benzene per unit dosage:

| Active ingredient | 200 g |
|---|---|
| Starch | 225 g |
| Ethyl cellulose | 5 g |
| Calcium carbonate | 1500 g |
| Magnesium Stearate | 25 g |
| Talc | 25 g |
| Silica | 20 g |
| for 10.000 tablets weighing | |

-continued each about 200 mg

Tablets containing 50 mg of 1-[N-methylpiperid-2yl] acetylamino 2-methoxy 5-trifluoromethyl benzene per unit dosage:

| Active ingredient | 500 g |
|---|---|
| Talc | 1200 g |
| Calcium carbonate | 300 g |
| Ethyl cellulose | 50 g |
| Magnesium phosphate | 430 g |
| Methyl cellylose (sold under the Trade Name of Methocel) | 25 g | for 10.000 tablets weighing about 250 mg

What we claim is:

1. A member of the group consisting of a compound of the formula

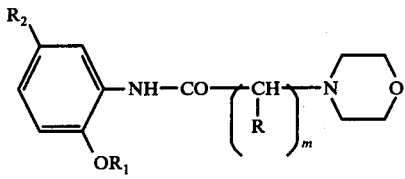

wherein:

m is 0 or an integer of 1 to 5

R is hydrogen or lower alkyl of 1 to 6 carbon atoms in the chain;

$R_1$ is lower alkyl of 1 to 6 carbon atoms, lower alkenyl of 1 to 6 carbon atoms, lower cycloalkyl of 3 to 7 ring carbon atoms or phenyl lower alkyl of 1 to 6 carbon atoms in the side chain;

$R_2$ is cyano, trifluoromethyl or lower alkanoyl of 1 to 6 carbon atoms; and the acid addition addition salts thereof with organic or mineral acids.

2. The acid addition salts of a compound of claim 1 with a mineral or organic acid.

3. 1-morpholinyl propionylamino)-2-methoxy-5-cyano benzene according to claim 1.

4. A composition active in inhibiting both gastric secretion and delay in gastric evacuation containing an inhibitorily effective amount of at least one compound of claim 1 in association with a pharmaceutical carrier or diluent.

5. A composition as claimed in claim 4 in any of the forms suitable for oral, parenteral, rectal, perlingual or percutaneous administration.

6. A composition as claimed in claim 4 containing from 10 to 200 mg of active ingredient per dosage unit.

7. A method of inhibiting gastric hypersecretion and delay in gastric evacuation which comprises administering to warm-blooded animals suffering or disposed to suffer from said ailment an inhibitorily effective amount of a compound of claim 1.

8. The method of claim 7 wherein the amount ranges from 0.3 to 6 mg/kg body weight per day.

* * * * *